United States Patent [19]

Qi

[11] Patent Number: 5,659,073
[45] Date of Patent: Aug. 19, 1997

[54] PROCESS FOR MAKING GLYCOL ETHER ACETATES

[76] Inventor: Jian Steven Qi, 95 Pepper Tree Dr. #7, Amherst, N.Y. 14228

[21] Appl. No.: 499,459

[22] Filed: Jul. 7, 1995

[51] Int. Cl.⁶ .................................................. C07C 67/24
[52] U.S. Cl. ........................................... 560/240; 560/239
[58] Field of Search ................................ 560/240, 239

[56]  References Cited

FOREIGN PATENT DOCUMENTS

| 0107020 | 5/1984 | European Pat. Off. . |
|---|---|---|
| 0 119 833 | 9/1984 | European Pat. Off. . |
| 56-020544 | 2/1981 | Japan . |
| 157 745 | 6/1992 | Poland . |
| 1290725 | 9/1972 | United Kingdom . |

*Primary Examiner*—Jose'G. Dees
*Assistant Examiner*—Rosalynd A. Williams
*Attorney, Agent, or Firm*—Richard D. Fuerle; Arthur S. Cookfair

[57] ABSTRACT

Disclosed is a method of making a glycol ether acetate. Acetic acid is reacted with a glycol ether at a molar ratio of about 1.1 to about 2, in a mixture with a catalyst and an azeotropic agent which can be either butyl acetate or dibutyl ether. The mixture is heated to a temperature and pressure sufficient to vaporize an azeotrope of water and the azeotropic agent. In another embodiment of the invention, a glycol ether acetate is made by preparing a reaction mixture of acetic acid and a glycol ether in a molar ratio of about 1.1 to about 1.2, about 5 to about 25 wt % n-butanol, an additional amount of acetic acid stoichiometric with the amount of n-butanol, and a catalyst. The reaction mixture is heated to form a glycol ether acetate, water, and butyl acetate. The azeotrope, excess acetic acid, butyl acetate, and glycol ether are successively removed by distillation.

23 Claims, No Drawings

PROCESS FOR MAKING GLYCOL ETHER ACETATES

BACKGROUND OF THE INVENTION

This invention relates to a process for making glycol ether acetates from acetic acid and a glycol ether. In particular, it relates to the use of a molar ratio of acetic acid to glycol ether of about 1.1 to about 2 and to the use of butyl acetate or dibutyl ether as an azeotropic agent.

Glycol ether acetates are generally manufactured by esterifying an ethylene glycol ether with acetic acid. To force the reaction to completion, the water by-product formed is removed using an agent that forms an azeotrope with water, known as an azeotropic agent or an entrainer. When the azeotrope is condensed, the entrainer must separate from the water so that the entrainer can be recovered and recycled.

Historically, toluene was used in industry as the entrainer. However, toluene is now regarded as a health hazard due to its toxicity, and tighter restrictions on the use of toluene have prompted manufacturers to replace it with hydrocarbons such as octane. Octane, however, does not work well for this system because, for unknown reasons, it carries over large amounts of the reactants (i.e., the glycol ether or acetic acid) with its water azeotrope, which then enter the waste water stream. This carryover can be as high as 30 wt % for acetic acid and 20 wt % for glycol ethers. The water often can be so contaminated with organics that its flash point is too low for safe handling, further increasing the disposal cost. Of course, this loss of raw materials significantly adds to the cost of manufacturing the acetate. Other water azeotrope solvents, such as p-xylene, ethyl benzene, 1-octene, heptane, and cyclohexane, for unknown reasons carried over at least 10 wt % organics no matter how the process conditions, such as the reflux ratios, were adjusted and they were much poorer entrainers.

SUMMARY OF THE INVENTION

I have discovered that butyl acetate and dibutyl ether are excellent entrainers in the reaction to form glycol ether acetates, provided that the molar ratio of acetic acid to glycol ether is about 1.1 to about 2. They form low boiling azeotropes (89° and 91° C., respectively) with water, but do not form azeotropes with the reactants or the glycol ether acetate product. Unlike toluene, butyl acetate and butyl ether are less toxic and safer to use, and they are better than octane because they entrain with water less than 5 wt % of the organics. Butyl acetate, under suitable conditions, entrains only 2% organics in the water stream.

The boiling points of butyl acetate (126.5° C.) and dibutyl ether (142° C.) are high enough to allow their separate distillation after the azeotrope has distilled, yet are sufficiently below the boiling point of any glycol ether acetate to be easily distilled off before the glycol ether acetate boils. The use of butyl acetate or dibutyl ether does not reduce the glycol ether acetate yield and the compounds are stable under the process conditions defined by this invention so that they can be reused. They are also non-corrosive and environmentally acceptable.

DESCRIPTION OF THE PREFERRED EMBODIMENTS

The glycol ether acetates of this invention are prepared by the reaction of acetic acid with a glycol ether. Glycol ethers can be made by reacting ethylene glycol with an alcohol, but commercially they are usually made by reacting ethylene oxide with an alcohol. For example, ethylene glycol monobutyl ether (EB) can be made by reacting ethylene oxide with butanol (BuOH):

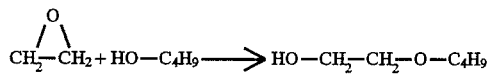

and ethylene glycol monobutyl ether acetate (EBA) can be made by reacting the EB product with acetic acid in the presence of a catalyst:

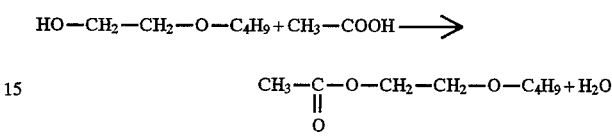

In addition to EBA, the other preferred glycol ether acetate products are ethylene glycol monoethyl ether acetate (EEA) and diethylene glycol monobutyl ether acetate (DBA), as they are widely used commercially.

Glycol ethers useful in this invention have the general formula

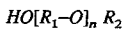

where $R_1$ is alkylene from $C_2$ to $C_{10}$, and is preferably alkylene from $C_2$ to $C_4$, and is most preferably ethylene as those compounds are used more commercially. In the formula, $R_2$ is alkyl from $C_1$ to $C_{10}$, and is preferably $C_1$ to $C_4$, and is most preferably ethyl or butyl as those are the more important commercial compounds; "n" is 1 to 3, and is preferably 1 or 2 for the same reason. Examples of glycol ethers include ethylene glycol monoethyl ether (also known as "Cellosolve"), ethylene glycol monomethyl ether (also known as methyl "Cellosolve"), propylene glycol monomethyl ether, ethylene glycol dibutyl ether (also known as dibutyl "Cellosolve"), ethylene glycol monohexyl ether (also known as n-hexyl "Cellosolve"), ethylene glycol monophenyl ether (also known as phenyl "Cellosolve"), diethylene glycol monoethyl ether (also known as "Carbitol"), diethylene glycol monomethyl ether (also known as methyl "Carbitol"), diethylene glycol diethyl ether (also known as diethyl "Carbitol"), diethylene glycol monobutyl ether (also known as butyl "Carbitol"), diethylene glycol dibutyl ether (also known as dibutyl "Carbitol"), and diethylene glycol monohexyl ether (also known as n-hexyl "Carbitol").

The glycol ether reacts stoichiometrically with acetic acid to produce the glycol ether acetate, but if butyl acetate is the azeotropic agent a molar ratio of acetic acid to glycol ether of about 1.1 to about 2 must be used to prevent the conversion of the butyl acetate to butanol. The presence of butanol significantly increases the organic content of the entrained water. For butyl ether, if a significant excess acetic acid is not used, large amounts (20%) of glycol ether are entrained with water. The reasons for this are not clear. Also, excess acetic acid is preferred because acetic acid can be distilled off more readily than the glycol ether. Preferably, about 15 to about 30 mole % excess acetic acid is used.

The reaction can be performed from about room temperature to about the boiling point of the reaction mixture. It is normally performed at about the boiling point in order to drive off the water that forms and thereby push the reaction to completion. For most glycol ethers, a temperature range of about 85° to about 120° C. is suitable, but the preferred reactant temperature is the temperature at which water is vaporized.

Sufficient butyl acetate or dibutyl ether entrainer should be used to form a good azeotrope mix in the overhead and to take up the volume in the distillation column plus the inventory in the condenser and water-organic separator. About 5 to about 25 wt % of the butyl acetate or dibutyl ether entrainer is preferred, based on the total weight of reactants. Less than about 5 wt % may be insufficient to efficiently remove all of the water formed and more than 25 wt % is usually unnecessary.

In a preferred embodiment of this invention, the butyl acetate entrainer is prepared in situ by the reaction of acetic acid with butanol

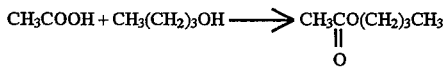

This is accomplished by simply adding butanol to the acetic acid and glycol ether mixture and using enough excess acetic acid to react stoichiometrically with the butanol. In this way, two acetates are prepared simultaneously, butyl acetate and a glycol ether acetate. If ethylene glycol monobutyl ether is used, the second acetate is ethylene glycol monobutyl ether acetate, and if diethylene glycol monobutyl ether is used, the second acetate is diethylene glycol monobutyl ether acetate.

A non-volatile catalyst is required in the method of this invention. While sulfuric acid, hydrochloric acid, chlorosulfuric acid, and phosphoric acid can be used, a sulfonic acid catalyst is preferred in industry because it is less corrosive. The sulfonic acid catalyst has the formula $$RSO_2OH$$

where R is hydrogen, alkyl from $C_1$ to $C_{15}$, or aryl, aralkyl, or aralkyl from $C_6$ to $C_{10}$. Examples of sulfonic acids that can be used include sulfonic acid (R=H), methane sulfonic acid (R=CH_3), benzene sulfonic acid (R=phenyl), and p-toluene sulfonic acid (R=tolyl). P-toluene sulfonic acid (PTSA) is preferred, as it has been found to work well. The amount of catalyst used is generally about 0.1 to about 0.5 wt %, based on the weight of the reactant charge. Less than 0.1 wt % catalyst may result in an unacceptably slow reaction rate, and more than 0.5 wt % may result in excessive corrosion of the equipment. The preferred amount of catalyst is about 0.1 to about 0.2 wt %.

The reactants and products are separated by distillation. The azeotrope of water and the entrainer distills off first. The azeotrope condensate separates into two phases in a separator and the organic phase is returned to the column to remove more water. After most of the water has been removed, acetic acid starts to come over followed by excess entrainer (i.e., butyl acetate or butyl ether), and finally, the glycol ether reactant.

The following examples further illustrate this invention.

EXAMPLE 1

A bench scale batch reaction system was set up to resemble an industry process for making EEA. The lab set up consisted of a 20 plate Oldershaw distillation column mounted on the center neck of a three-neck 1000-mL round bottom flask. The flask served as a still pot and reactor. A condenser and a 20-mL Dean-Stark receiver were installed on the top of the column. The Dean-Stark allowed phase separation and continuous return of the lighter phase back to the top of the column.

Charged into the pot were 225 g (2.5 moles) of ethylene glycol monoethyl ether (EE), 165 g (2.75 moles) of acetic acid (HAc), 0.55 g of PTSA, and 60 g of butyl acetate (BuAc). The acetic acid charge was 10 mol % excess. After the mixture was heated to reflux for one hour at an overhead temperature of 89° C., the distillate of entrainer/water mixture was collected and settled down into two phases in the Dean-Stark receiver, where the upper organic phase overflowed back into the top of the column. Small quantities of water were drained from the bottom of the Dean-Stark to maintain about 19 mL of water and 5 mL organic phase in the receiver. The overhead temperature rose as water in the column was being depleted. When the overhead temperature reached 101° C., the water removal step was completed and the column was put under total reflux. A total of 43.8 g of water, out of 45 g generated totally by reaction, were removed. The water cuts were analyzed by gas chromatography (GC) and were found to contain 1 wt % butanol and about 2 wt % total organics.

The Dean-Stark was replaced by a K-head adapter equipped with automatic reflux control. The entrainer and the excess reactant were collected as intermediate cuts at reflux ratios ranging from 1:1 to 9:1. Finally, 211.3 g pure product was obtained at 1:3 reflux ratio. The complete results are given in the table below. The composition of each cut was analyzed by GC, whereas the acetic acid value was determined by the ASTM D1639 titration method. The quantity of EEA obtained was 54 wt % of the total reactants charged. This met the productivity standard used by industry.

| Steps | Pot Temp (°C.) | Overhead Temp (°C.) | Reflux Ratio | Wt of Cuts (grams) | Cut Composition |
| --- | --- | --- | --- | --- | --- |
| Heating up | 14 → 116 | 14 → 89 | — | | |
| Reaction 1 hr | 116 → 114 | 89 → 90 | Total | | |
| Water Removal | 114 → 145 | 90 → 95 | Only organic layer returned to top of column | 40.5 | 1% BuOH, 0.5% BuAc, 0.2% EE |
| | 145 | 95 → 91 | Total Reflux 0.7 hr | | |
| | 145 → 146 | 91 → 101 | Only organic layer returned to top of column | 3.3 | 1% BuOH, 1.4% HAc, 2.6% BuAc |
| Total Reflux 0.5 hr | 146 → 147 | 101 → 93 | Total | | |
| Intermediate | 146 | 93 → 116 | 1:1 | 4.3 | (Two Phases) |
| Cuts (removal of entrainer & excess HAc) | 146 → 153 | 116 → 130 | 6:1 | 70.9 | 18% HAc, 75% BuAc, 3% EE, 2% EEA |
| | 153 | 130 → 124 | Total Reflux 0.5 hr | | |
| | 153 → 155 | 124 → 155 | 9:1 | 20.9 | 6% HAc, 30% BuAc, 4% EE, |

-continued

| Steps | Pot Temp (°C.) | Overhead Temp (°C.) | Reflux Ratio | Wt of Cuts (grams) | Cut Composition |
|---|---|---|---|---|---|
| | 155 | 155 | 9:1 | 30.5 | 60% EEA, 5100 ppm HAc, 1.4% BuAc, |
| | 155 | 155 | 9:1 | 10.8 | 98.5% EEA 928 ppm HAc, 0.2% BuAc, |
| | 155 | 155 | 9:1 | 22.3 | 99.5% EEA 575 ppm HAc, >99% EEA |
| Product Cut | 155 → 160 | 155 → 156 | 1:3 | 211.3 | 99 ppm HAc >99% EEA |
| Pot Bottom | | | | 36.9 | |

EXAMPLE 2

This example is similar to Example 1 except that 50 mole % excess acetic acid was used (310 g of EE and 312 g of acetic acid were charged). The water removed contained less than 0.5 wt % butanol. Other cuts were similar to those in Example 1.

EXAMPLE 3

This example is similar to Example 1 except that 25 mole % excess acetic acid was used. The water removed contained less than 0.8 wt % butanol. Other cuts were similar to those in Example 1.

EXAMPLE 4 (COMPARATIVE)

This example is similar to Example 1 except that butyl acetate was replaced by octane. The first cut of water was less than 10% of total water to be removed but contained 30 wt % acetic acid. The experiment was stopped at that point. If excess EE was used, the water obtained contained 25% EE.

EXAMPLE 5 (COMPARATIVE)

The setup was similar to that in Example 1. About 127 g acetic acid, 210 g ethylene glycol ethyl ether (about 10 mol % excess), 64 g butyl acetate, and 0.6 g PTSA were charged into the pot. After boiling the contents at 106° C. for 90 minutes, a sample taken from the pot indicated 25 wt % of the butyl acetate had been converted to butanol. The first water cut of less than 1 gram contained 4.5% butanol, 1% butyl acetate, and more than 1% acetic acid. This example shows that excess acetic acid must be used to prevent decomposition of butyl acetate by hydrolysis and transesterification and loss of butanol.

EXAMPLE 6

The procedure was similar to Example 1. In this example, ethylene glycol monobutyl ether acetate (EBA) was synthesized using butyl acetate entrainer. Ten percent excess acetic acid was used. To avoid high process temperatures, vacuum distillation was used. To study the recyclability of the entrainer, the still pot bottom residue and intermediate cuts that contained the excess acetic acid and butyl acetate were reused for a second batch. In the second batch, 40 grams of still bottom containing PTSA catalyst and 100 grams of intermediate cuts which contained the 10 mol % excess HAc from a previous run were recycled along with an equal molar charge of acetic acid and EB (2.05 moles or 243 g EB and 137 g acetic acid). The results were the same as the first batch. The pure product obtained was 60 wt % of the total material charged. The table below summarizes the results.

| Steps | Pot Temp (°C.) | Overhead Temp (°C.) | Press (mmHg) | Reflux Ratio | Wt of Cuts (grams) | Cut Composition |
|---|---|---|---|---|---|---|
| Heating up | 17 → 117 | 18 → 76 | 500 | — | | |
| Reaction 1 hr | 116 → 108 | 75 | 500 | Total | | |
| Water Removal | 108 → 143 | 75 → 87 | 500 | Only org layer returned to top of column | 32 | 1% BuOH, 0.5% HAc, 0.5% BuAc |
| | 144 | 87 → 74 | 500 | Total reflux 0.2 h | | |
| | 144 → 148 | 74 → 87 | 500 | Only org layer returned to top of column | 2.4 | 7% HAc, 1% BuAc |
| Total Reflux 0.5 hr | 139 | 69 | 340 | Total | | |
| Removal of | 140 | 69 → 79 | 340 | 1:1 | 8.6 | (Two Phases) |
| Entrainer & Excess HAc | 140 → 161 | 79 → 135 | 340 | 6:1 | 75.6 | 20% HAc, 75% BuAc, 3% EB, 1% EBA |
| | 135 | 110 | 134 | Total reflux 0.5 hr | | |
| | 135 | 110 → 121 | 134 | 9:1 | 9.8 | 13,527 ppm HAc |
| | 135 | 121 → 128 | 134 | 9:1 | 8.8 | 2463 ppm HAc |
| | 135 | 128 → 131 | 134 | 9:1 | 13.7 | 605 ppm HAc |
| | 135 | 131 | 134 | 9:1 | 7.2 | 270 ppm HAc |
| Product Cut | 135 | 131 → 136 | 134 | 1:3 | 301 | 41 ppm HAc, 100% EBA |
| Pot Bottom | | | | | 40 | |

EXAMPLE 7

This example is similar to Example 6. However, diethylene glycol monobutyl ether acetate (DBA) was synthesized using a butyl acetate entrainer. About 25 mol % excess acetic acid was used. The butyl acetate charge was about 11 wt % of total reaction mixture. Due to the high boiling points of DB and DBA, the process was conducted under vacuum. The water removal step was conducted at 400 mmHg, the acetic acid and butyl acetate distillation at 60 mmHg, and product DBA distillation at 20 mmHg to maintain the pot temperatures below 160° C. Other conditions were similar to those in Example 6. The yield and composition obtained were also similar to those in Example 6.

EXAMPLE 8

This example is similar to Example 3 except that butyl acetate was replaced by n-butyl ether. The water obtained contained no n-butyl ether, 3 wt % EE and 2 wt % acetic acid. Other cuts were similar to those in Example 3. In this example, 25 wt % excess acetic acid was used. When the charge ratio was reversed, the water contained 20 wt % EE. Therefore, n-butyl ether is a good entrainer only when excess acetic acid is present.

EXAMPLE 9

Two 50 mL 2-neck round bottom flasks were set up with two condensers on their tops. The first flask was charged with 23 g EE, 23 g acetic acid, 0.2 g PTSA, and 7 g butyl acetate, while 23 g EE, 26.6 g acetic acid, 0.2 g PTSA, and 4.4 g butanol were charged into the second. After heating both pots to refluxing (107° C.) for one hour, a GC analysis showed almost identical compositions for both mixtures. Little change in composition occurred after one additional hour of heating. Both mixtures at this point consisted of about 50 wt % EEA, 20 wt % acetic acid, 9 wt % EE, 13 wt % butyl acetate, 7 wt % water, and less than 1% butanol. Apparently, in the second flask 3.6 g acetic acid had reacted with 4.4 g acetic acid to form about 7 g butyl acetate and 1 g water. This example demonstrates that a butyl acetate entrainer can be generated in situ and the two acetates can be produced simultaneously.

EXAMPLE 10

In this example, various entrainers were tested for removing water from acetic acid/water or EE/water mixtures. To test an entrainer for removing water from an acetic acid/water solution, about 100 grams of acetic acid, 100 grams of water, and 60 grams of an entrainer were charged into the distillation set-up described in Example 1. The mixture was then brought to total reflux. After the overhead temperature stabilized at the azeotrope boiling point, a small overhead condensate cut (less than 5% of the total charge in size) was collected and decanted. The aqueous layer was analyzed by GC for the amount of total organic and acetic acid carryover. The same experiment was also done for an EE/water mixture. The table below summarizes the organic carryover for each entrainer tested.

| Entrainer | Overhead Temperature (°C.) | Organic In Overhead Aqueous Phase | |
|---|---|---|---|
| | | For Acetic Acid-Water Mixture (wt % HAc) | For EE-Water Mixture (wt % EE) |
| n-Octane | 89 | >20 | 25 |
| 1-Octene | 88 | 11 | 12 |
| Heptane | 79 | 20 | 18 |
| Cyclohexane | 68 | 21 | 11 |
| p-Xylene | 90 | 10 | 12 |
| Ethylbenzene | 91 | 15 | 10 |
| Chlorobenzene | 89 | 14 | 4 |
| n-Butyl Acetate | 90 | 2 | 0 |
| n-Butyl Ether | 91 | 1.5 | 20 |

This example shows that butyl acetate is the best entrainer of the solvents tested and that excess acetic acid is necessary when butyl ether is used as the entrainer.

I claim:

1. A method of making a glycol ether acetate comprising
    (A) reacting acetic acid with a glycol ether at a molar ratio of about 1.1 to about 2 in a mixture with a catalyst and an azeotropic agent selected from the group consisting of butyl acetate and dibutyl ether; and
    (B) heating said mixture at a temperature and pressure sufficient to vaporize an azeotrope of said water and said azeotropic agent.

2. A method according to claim 1 wherein said molar ratio is about 1.15 to about 1.30.

3. A method according to claim 1 wherein said glycol ether is ethylene glycol ethyl ether.

4. A method according to claim 1 wherein said glycol ether is ethylene glycol monobutyl ether.

5. A method according to claim 1 wherein said glycol ether is diethylene glycol monobutyl ether.

6. A method according to claim 1 wherein said azeotropic agent is dibutyl ether.

7. A method according to claim 1 wherein said azeotropic agent is butyl acetate.

8. A method according to claim 7 wherein said butyl acetate and said glycol ether acetate are prepared in the same pot by reacting acetic acid with butanol and said glycol ether, respectively.

9. A method according to claim 1 wherein said catalyst is p-toluene sulfonic acid.

10. A method according to claim 1 including the additional step of distilling off excess acetic acid.

11. A method of making a glycol ether acetate comprising
    (A) reacting acetic acid with a glycol ether in a molar ratio of about 1.1 to about 2 in a mixture with about 0.1 to about 0.5 wt % p-toluene sulfonic acid and about 5 to about 25 wt % butyl acetate;
    (B) heating said mixture at reflux to distill off a butyl acetate-water azeotrope;
    (C) separating said butyl acetate from said butyl acetate-water azeotrope;
    (D) returning said separated butyl acetate back to step (B); and
    (E) additionally heating said mixture to distill off excess acetic acid.

12. A method according to claim 11 wherein said glycol ether is ethylene glycol ethyl ether.

13. A method according to claim 11 wherein said glycol ether is ethylene glycol monobutyl ether.

14. A method according to claim 11 wherein said glycol ether is diethylene glycol monobutyl ether.

15. A method according to claim 11 wherein said butyl acetate and said glycol ether acetate are prepared in the same pot by reacting acetic acid with butanol and said glycol ether, respectively.

16. A method according to claim 11 wherein said reaction is at about 85° to about 120° C.

17. A method according to claim 11 wherein said molar ratio of acetic acid to glycol ether is about 1.15 to about 1.30.

18. A method of making a glycol ether acetate comprising
 (A) preparing a reaction mixture which comprises
  (1) acetic acid and a glycol ether selected from the group consisting of ethylene glycol ether, diethylene glycol ether, and propylene glycol ether in a molar ratio of about 1.1 to about 2;
  (2) about 5 to about 25 wt % n-butanol, based on total reactants weight;
  (3) an additional amount of acetic acid stoichiometric with the amount of said n-butanol; and
  (4) a catalyst;
 (B) heating said reaction mixture to form a glycol ether acetate, butyl acetate, and water;
 (C) removing by distillation an azeotrope of water and butyl acetate;
 (D) separating butyl acetate from said azeotrope;
 (E) returning said separated butyl acetate to step (C);
 (F) removing by distillation excess acetic acid;
 (G) removing by distillation excess butyl acetate; and
 (H) removing by distillation said glycol ether.

19. A method according to claim 18 wherein said glycol ether is ethylene glycol ethyl ether.

20. A method according to claim 18 wherein said glycol ether is ethylene glycol monobutyl ether.

21. A method according to claim 18 wherein said glycol is diethylene glycol monobutyl ether.

22. A method according to claim 18 wherein said molar ratio is about 1.15 to about 1.30.

23. A method according to claim 18 wherein said catalyst is p-toluene sulfonic acid.

* * * * *